(12) United States Patent
Shinnick (10) Patent No.: US 11,771,894 B2
(45) Date of Patent: Oct. 3, 2023

(54) APPARATUS AND METHOD FOR RESTORING HEALTH VIA ENERGETIC FIELD

(71) Applicant: Phillip Shinnick, New York, NY (US)

(72) Inventor: Phillip Shinnick, New York, NY (US)

(*) Notice: Subject to any disclaimer, the term of this patent is extended or adjusted under 35 U.S.C. 154(b) by 40 days.

(21) Appl. No.: 16/888,713

(22) Filed: May 30, 2020

(65) Prior Publication Data
US 2021/0370061 A1    Dec. 2, 2021

(51) Int. Cl.
*A61N 1/36*      (2006.01)
*A61N 1/40*      (2006.01)

(52) U.S. Cl.
CPC ............ *A61N 1/36014* (2013.01); *A61N 1/40* (2013.01)

(58) Field of Classification Search
CPC ........ A61N 1/36014; A61N 1/40; A61N 1/10; A61N 1/44; A61H 1/00
See application file for complete search history.

(56) References Cited

U.S. PATENT DOCUMENTS

2014/0343642 A1* 11/2014 Lauer ................... H05K 9/0001
607/115

* cited by examiner

*Primary Examiner* — Mark W. Bockelman
(74) *Attorney, Agent, or Firm* — UNIPAT.ORG; Anne C. Avellone; David M. Geshwind (57) ABSTRACT

A device for providing an energetic field to promote the body's self-healing process comprises electronics immersed in a dialectric oil in a first enclosure which accelerate and spin an energetic current within a gas-filed glass tube. The tube protrudes through a small opening into a second large metal (e.g. copper)-lined patient enclosure, such that the energy emitted from the tube is directed toward a circular concave baffle covered in a densely woven fabric. A plastic sheet optionally protects the patient from arcing with the baffle. Seating/support is provided to properly position the patient; as well as seating for the practitioner/therapist who both positions the patient, and provides mental and emotional guidance, to optimize patient receptivity to treatment.

20 Claims, 8 Drawing Sheets

APPARATUS AND METHOD FOR RESTORING HEALTH VIA ENERGETIC FIELD

CROSS-REFERENCE TO RELATED APPLICATIONS

The instant application claims priority from provisional application 62/921,078, filed May 30, 2019 which is hereby incorporated, in its entirety, by reference.

COPYRIGHT NOTICE

This patent document contains material which is subject to copyright protection. The entire specification is copyright to applicant. The copyright owner has no objection to the facsimile reproduction by anyone of the patent document or the patent disclosure, as it appears in the Patent and Trademark Office patent file or records, but otherwise reserves all copyright rights whatsoever. In particular, the graphics, designs and text herein, in addition to any patent rights, are also covered by copyright and/or trademark. Permission to copy those materials is solely limited to their use in conjunction with the lawful distribution of this patent document and all other rights, including their publication, adaption, compilation, or other uses are reserved. No such use can be made without the written permission of the copyright holder and cannot be made with proper notice and compensation.

BACKGROUND OF THE INVENTION

Field of the Invention

Generally, the instant invention relates to a device and process designed to aid an ailing individual's body to heal itself.

DESCRIPTION OF RELATED ART AND SCOPE OF INVENTION

Octagonal and rectilinear reciprocal coupling in space creating non-zero mass and spin-1 according to Lorentz's interpretation, creates a template for earth's cavity and transverse lighting shock waves according to Tesla from an extrapolation of non-zero space. The consequences of non-zero-positive mass are explored. Obolensky from this inspiration created a miniature Tesla Magnifying Transmission which organizes water, creates emanations of acupuncture points, and improves disease conditions. Bose-Einstein condensation parallels of inorganic Helium at low temperatures and organic human global physiological measurements of Zen Master meditators show properties of Oneness. European science does not have a philosophical history of curvilinear and rectilinear understanding of the human mind/body consciousness to the aether field, internal organs and energy flow within the body. Turning to the Natural philosophy of the Orient provides a way that the fragmented physiological and mental habits can be changed to a more unconditioned or phase change natural state through Qigong curvilinear and transverse breathing practices both inside the organism and interacting with the outside to gain energy and overcome disease.

BRIEF DESCRIPTION OF DRAWINGS

FIG. 11 (FIGS. 11A through 11G) depict various internal and external practices whereby Universal Qi (density matrix non zero matter and spin 1) can be accessed through practices of bringing in outside universal Qi through the breath.

DESCRIPTION OF INVENTION

A device and process are designed to aid an ailing individual's body to heal itself. By preparing the patient via counseling, meditation, visualization and the like, the patient is put in a more receptive state to benefit from the healing process.

The patient is placed within a metallic (e.g., copper)-lined enclosure (essentially a Faraday cage) and placed in a comfortable and/or therapeutically beneficial position, seated, reclining, standing or otherwise.

Optimally the patient enclosure is maintained at or near a temperature of 90 degrees F., and at or near a relative humidity of 85%.

Transformers and coils immersed in a dielectric oil in a separate enclosure, which is outside the patient enclosure, accelerate and spin an energetic current to create a high-voltage, rapidly modulated current within a gas-filled glass tube, one end of which protrudes into the patient enclosure through an opening. The energy emitted from the tube is directed toward a dome or circular concave baffle covered in a densely woven fabric which disperses an energetic field within the enclosure.

A plastic sheet, optionally with embedded nano-particles, is optionally placed between the dome and the patient to eliminate potential arcing between the dome and the patient.

The energy field thus created inside the room assists the patient's own natural energetic properties (e.g., Qi) to promote a restoration of a healthy and balanced state.

The body's tendency to achieve self-healing (i.e., restore a state of properly balanced and free flowing energy) is encouraged by immersion in this field, in ways that are similar to those promoted by practitioners of healing arts such as acupuncture, medical acupuncture, deep needling, Qigong, and the like.

Seating or other supports are provided within the patient enclosure to enable proper positioning of the patient so that the energy emitted from the tube can be directed toward the area to be treated.

Seating is optionally provided for the practitioner/therapist to accompany the patient during therapy, to provide proper alignment of the patient and the apparatus. And, also to provide to the patient, mental and emotional guidance, in order to promote optimal receptivity of benefit by the patient.

Figure 12:
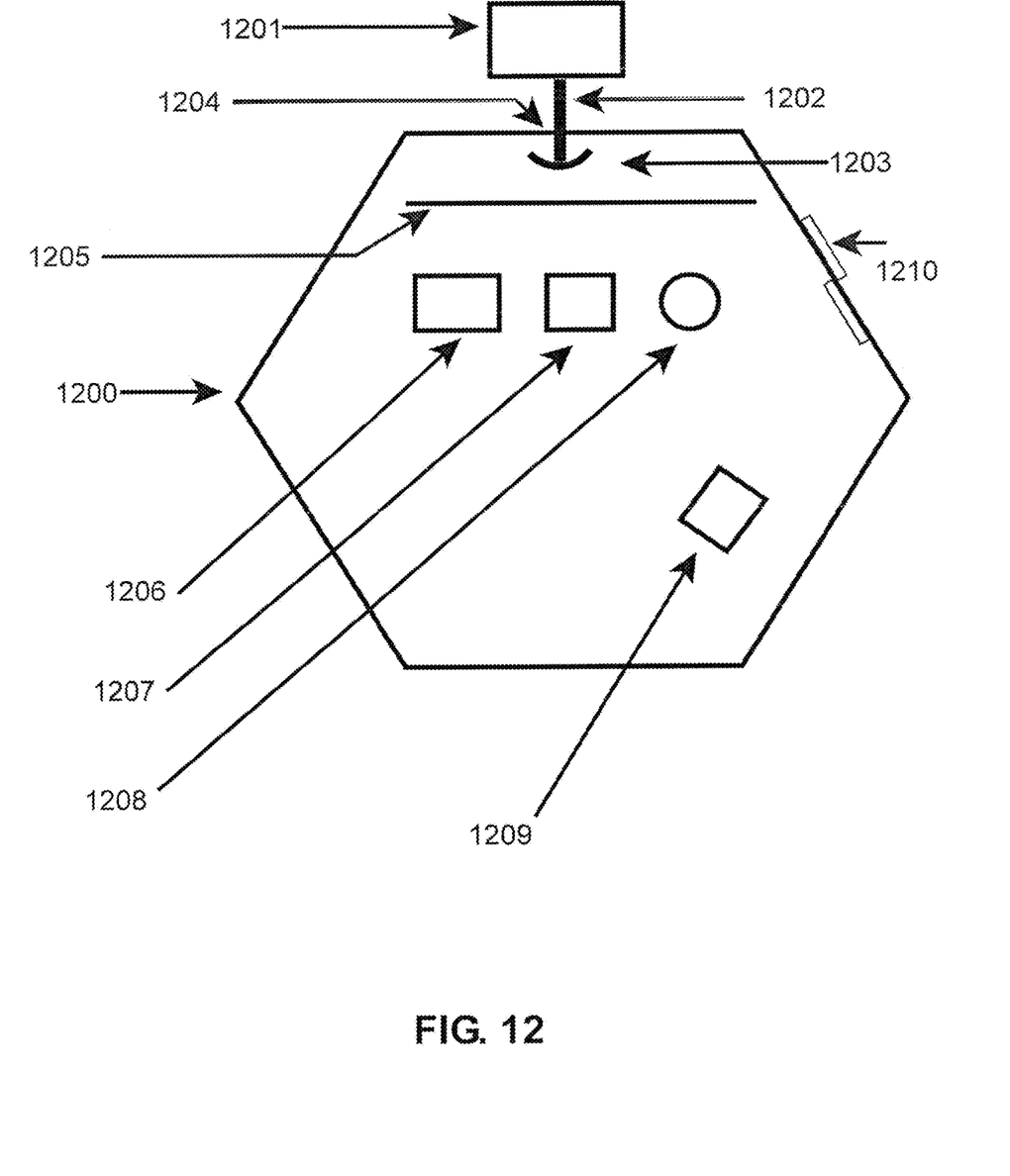
FIG. 12 depicts the internal and external features of the treatment device.

FIG. 12 depicts the preferred embodiment of the instant invention comprising: Element 1200, an external enclosure of the treatment device, the walls, floor and ceiling of which are composed of a layer of metal (e.g., copper) and a layer of an insulating material; Element 1201, a dielectric-oil-filled housing for electrical circuits; Element 1202, a glass gas-filled cylinder; Element 1203, a dome approximately 18 inches in diameter which is wrapped in tightly woven fabric; Element 1204 an opening for cylinder 1202 to pass from the housing 1201 through the wall of the enclosure into the enclosure 1200; Element 1205, a movable plastic screen separating the disc from the treatment area of the enclosure; Elements 1206, 1207 and 1208, a bench, chair and stool, respectively, any of which may be placed in the enclosure to enable the particular area of the patient to be treated to be appropriately located in relation to the therapeutic field that is generated; Element 1209 optional seating for the person administering the therapy to the patient; and, Element 1210, sliding doors to allow entrance and egress to/from the enclosure.

Theoretical Basis of Invention and Technical Details

What follows are technical details, as well as a discussion of the scientific theory underpinning the invention, and a discussion of clinical findings.

The theoretical model postulated by Obolensky and Vigier resulting from Lorentz's views is to consider light, i.e., Maxwellian fields, as made up of real, spinning extended photons with spin-1 and non-zero mass linked to real elements in a carrying continuous flat three-dimensional real infinite aether field.. sup. [i][ii][iii] This moving aether thus contains (carries) a chaotic distribution of field-piloted extended solitons and wave elements, i.e., piloted solitons {Soliton: Phase conjugate energy density, reciprocally orthogonal spin coupled rectilinear vibration of transverse Hertzian waves, double density 120 Pi (377 ohm) space impedance, the variable KdV energy density Solitary Wave equation determinants of space impedance.}} which can be describe by collective Maxwellian equations, locally invariant under $SU_{(2)}$ for vortices' filling this flat unlimited, three dimensional space. In Lorentz's model, observers, and measuring devices are both made up of aether elements.[iv] [v] [vi] [vii]

The key idea is that the aether has density from the intersection of transverse and longitudinal fields or coulombic and gaussian field intersecting.[vii] This density can also be evaluated by the heaviness of rotating bodies the resistance offered to their rotation. The acceleration of gravity at the surface of a rotating body at its equator can be calculated from known values of the gravitational force F and equatorial radius $R_e$ by $$G = F/\Pi R_e^2$$

its velocity at the equator if not retarded by the weight would be $$Vg = \sqrt{(gR_e)}$$

A measurement of the sidereal period given the actual velocity at the equator $V_e$. The equator's acceleration ae can then be calculated by the expression $V_e^2/R$. The ratio $g/a_e$ is a measurement of the rotating body's heaviness.

If we assume that inertia is the tendency of an object to maintain its state of uniform motion, then inertia can be described as a resistance to change of motion of a given body, so it is proportional to the body's local weight W. Thus W=ma (a has superscript of—for inertia) This formula is confirmed by experiments that show that inertia is independent of the mass. This implies that the mass and its orbital rotation velocity vary when its velocity changes. For example, the angular velocity w of Earth's spin is not the same at perihelion (which occurs January 1-4), i.e. 6.231. 10 neg 3 m.s. neg. 2, and at aphelion (July 4-6), i.e., 5.6637. 10 neg. 3 m.s. neg2 where the Earths acceleration, i.e., weight is different. This has been verified by the observation of Essen, which shows that the time rotation of the Earth in terms of the cesium atomic standard is faster~ in July and slower in January F.A.P.P. The Earth weighs less in aphelion than in perihelion and offers less resistance to it angular velocity. {{P. Spolter. "Gravitational Force of the Sun." Orb. Publishing Co., 11862 Balboa Blvd, Granada Hills, Calif. 91344-2753 USA (1993) and B. Margon. Physics Today 7 (1960), 26}}

Heat and movement create change of inertia and weight.

Accepting Lorentz's point of view, one assumes that Maxwell's waves describe nonzero-mass, spin-1, extended vortices moving in a Dirac-type continuous vacuum. They can individually be described by (1) a center of mass carrying an internal spin with $E=hv=mc^2$ (2) two centers of electromagnetic charge at the two extremes of a diameter perpendicular to the photon's spin where these two localized associated charges, e− and e+ rotate on themselves with an angular momentum h/2.

Carey argues; a detailed analysis of the transverse Doppler shift of the spectral results of the stellar object S.S. 433 in terms of the Lorentz model shows that it predicts that its stellar spectra and pulsar rates will have a second-order Doppler cycle with a period of one year and an amplitude of approximately 2 part in 10,000. The source S.S, 433 is some 12,000 light years distant and is emitting jets at 26% of the velocity of light as discovered by Margon.[ix] The orientation of its jets goes through a cycle so that every 164 days the jets are traveling exactly at right angles to the line of sight. At these times the jets show a transverse Doppler shift corresponding to that expected of the Lorentz theory for a velocity of 0.26c, since the vector of Earth's net velocity with respect to the 2.7 K microwave background lies in the same plane as its orbit around the sun, this implies that the Earth's net velocity oscillates by ±30 km per second with an annual cycle. Lorentz's Relativity Model thus also predicts that after correction for the usual first-order Doppler effects (red), second-order Doppler effects (blue) will show an effect having an amplitude of about two parts in 10,000 and a period of one year.

The Consequences of Non-Zero-Positive Mass

If the mass is small enough, it implies a practical (FAPP) separation of the transverse (with spin $J_3=\pm 1$) from the longitudinal ($J_3=0$) Maxwellian waves. The former ($J_3=\pm 1$) are transverse waves moving with velocity <c, the latter corresponding to a static, Coulombic-type field exp(−muRµ)/Rµ, Rµ denoting the distance to the central point in a rest frame of the center of charge Xµ.

a) The pilot fields surround particle-like photons in such a way that their internal orbital motion beat in has around the axis defined by heir charge orbital momenta.

b) in their rest frames (centered on Xµ) longitudinal photons are static (i.e., $\Delta X\mu=\gamma^2 X\mu$) and their charge distribution is flattened along Xµ in any other Lorentz frame according to the laws of Special Relativity Theory.

c) Photons are present only with transverse electromagnetic waves, and their energy-momentum is carried by photons and by waves.

d) This also implies that a moving, limited source containing electrons: 1) Is surrounded by a real, physical, limited Coulombic-type field that corresponds to a superposition of all the Coulombic transverse electronic fields with $J_3=0$ in their rest frames. The field (a) contains no photons and has limited extension around the source 2) Will emit longitudinal waves ($J_3=0$) from their accelerated motions.

Extended electrons (or positrons) are also contained in the Dirac-type aether. They are made up of localized, extended sub-elements defined by a center of mass Yµ. (with $E=h\nu=mc^2$) and a different center of charge Yu around which an electronic charge distribution rotates. This center spirals around Yµ at a Compton distance, with a velocity ≈c. The electromagnetic charge rotates on itself with an angular momentum h/2.

In this model, electrons are extended bilocal structures (made up of a hole and a bump in Dirac's aether), which contain different angular momentum around Yµ and Xµ, the latter surrounded by rotating charge and mass distributions.

Localized photons and electrons elements are embedded in an aether, which moves in flat-space. The aether satisfies locally the laws of Special Relativity (with measurement instruments included) but their accelerated elements' motions do not satisfy the laws of General Relativity and change their shape in accelerated motions (detected by real local, aether-built elements) in the flat space in which they move.

Longitudinal and Transverse: Curvature Earth and Transverse Lightening, Tesla's Extrapolation of Non-Zero Space Tesla, in the early 1900's was the first to have determined that the earth/ionosphere wave cavity was stimulated by atmospheric electricity. He believed this resonance was the key to aerial transmission of electrical power. Years later, the resonant properties of our terrestrial wave cavity are generally credited to German physicist W. O. Schuman and Konig in 1954. The first spectral representation of this phenomenon was prepared by Balser and Wagner in 1960.

There is a "cavity" defined by the surface of the Earth and inner edge of ionosphere 55 kilometers up. At any moment, the total charge residing in this cavity is 500,000 Coulombs. There is a vertical current flow between the ground and the ionosphere of 1-3×10 L-12 Amperes per square meter. The speed of light is 186,000 miles per second and the circumference of the Earth is 24,000 miles. That means that an electrical impulse from a lightning strike will travel around the Earth approximately ~8 times per second (186/24=7.75).

There are about 1000 lighting storms at any given moment worldwide. Each produces 0.5 to 1 Ampere and they collectively keep the Earth's electromagnetic' cavity circulation active. These so-called Schuman Resonance are quasi standing electromagnetic waves, like waves on a spring that have to be 'excited' to be observed. They are not caused by anything internal to the Earth, its crust or its core. They naturally occur at specific frequencies between 6 and 50 cycles per second: specifically, 7.8, 14, 20, 26, 33, 39, and 45 Hertz, with a periodic variation of about 0.5 Hertz.

This daily variation appears to be a function of the height of the ionosphere and solar activity. So long as the properties of Earth's electromagnetic cavity remain the same, these frequencies remain the same. Presumably there is also variation due to the 11-year solar activity cycle.

Tesla built in Wardencliffe station a World System of Wireless Transmission of Energy with Coulombic-field electrodes 285' high and 85' elliptical geometry reportedly supported 25 Mv scaler transitions. An oversimplified idea of Tesla was to create an energy which skips on density matrix in the cavity of the earth with more energy emerging than was putt in. For further investigation of the superluminal Coulombic field's dynamic permittivity see http://www.energyscience.co.Le27/notes.html {{In the Berlin Lecture it was suggested that a capacitor, particularly one of concentric cylinder electrode construction, might deliver an output, when discharging, an amount of energy that could be much as double that supplied as input when charging. This might seem to pose a problem with regard to the conventional mathematical analysis of capacitor properties, bearing in mind that we assume that the charge input Q is equal to the capacitance C multiplied by voltage V . . . . In short, it had be effective permittivity of the dielectric properties of the capacitor that changes to deliver the extra energy as output.}} and R. Antanasijevic et al[x] The last century of required "fatal" entropy teaching ignored Tesla's fundamental more efficient adiabatic energy transmission to perpetuate the existing 50% maximum-energy-transfer" technology. By requiring equilibrium thermodynamics and its "fatal" second law, this obsolete technology exacerbates global warming. Ilya Prigogine won his Nobel Prize by proving that far-from-equilibrium thermodynamics and adiabatic engineering can effectively circumvent the second-law-required entropy-gain that excuses the short-term economic benefit by wontedly dissipating more than 50% of our fuel's total energy into the global environment as heat waste.

Upon Tesla's death, the US Government seized his papers on his Magnifying Transmitter which made adiabatic energy-transmission possible. After Tesla understood the financial barriers to wireless electric power, he prepared but did not submit a definitive patent application. Obolensky went to Belgrade and found among the voluminous archives of at the Nikola Tesla Museum Belgrade the image found in FIG. 2.

Figure 3:
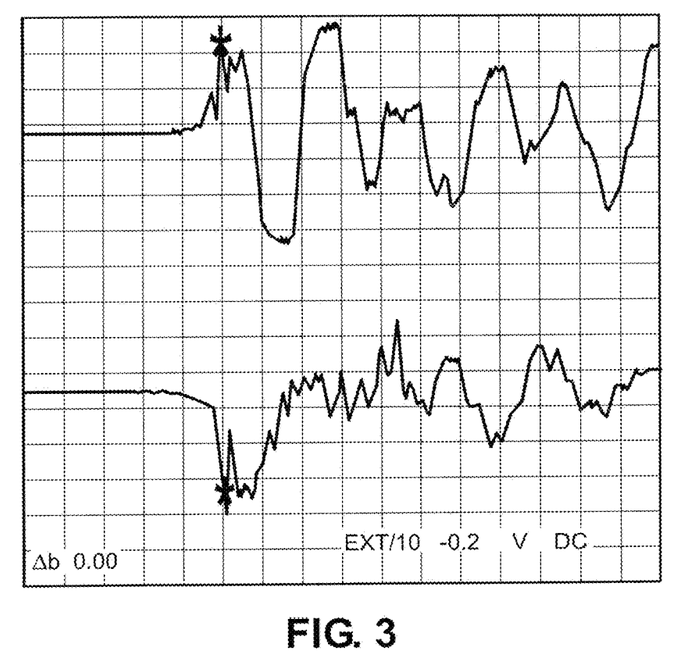
FIG. 3 depicts the superluminal propagation of the Coulombic field from Obolensky's Miniature Magnifying Transmission of superluminal energy propagation shown in the Coulombic currents detected by identical antenna systems.
Figure 13:
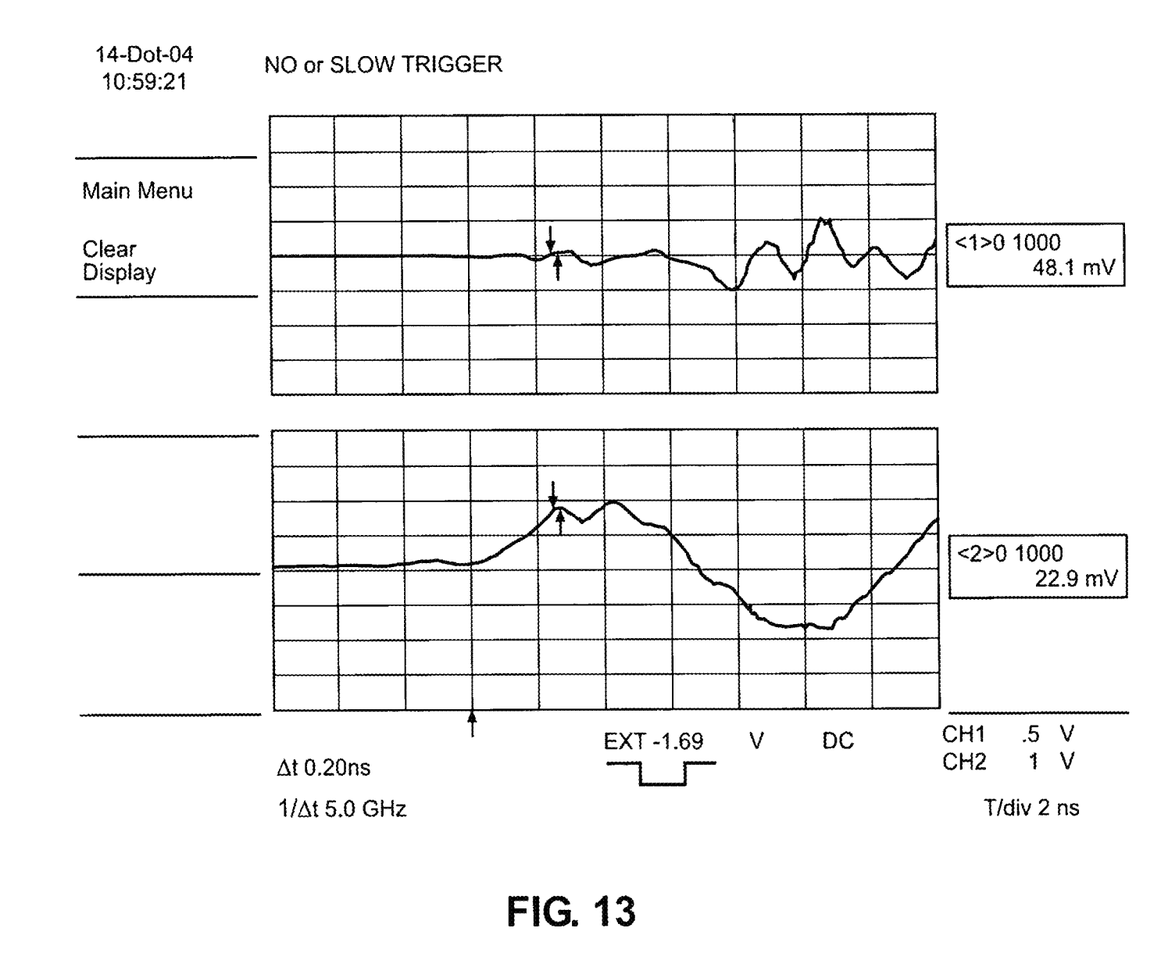
FIG. 13 depicts an oscilloscope image measuring light speed from co axial sensors within the miniature Tesla Magnifying Transmission in 2004. This shows a superluminal velocity, then variations in speed.

FIG. 3 demonstrates superluminal propagation of the Coulombic field from Obolensky's Miniature Magnifying Transmission. of superluminal energy propagation shown in the Coulombic currents detected by identical antenna systems. The effect antenna's 4.25' distance from the dome (lower trace) should produce a 4.25 ns light speed delay. However, the observed coincidence of the dome's causal earth-current indicates a superluminal velocity. A spike of superluminal velocity and then after lesser rates. Variations in the speed of light. This confirms what Tesla wrote. FIG. 13 constitutes another measurement that the inventor and Obolensky conducted in 2004 with slightly different oscilloscope setting.

Obolensky's Experimental Miniature Tesla Magnifying Transmission Instrument.

Figure 1:
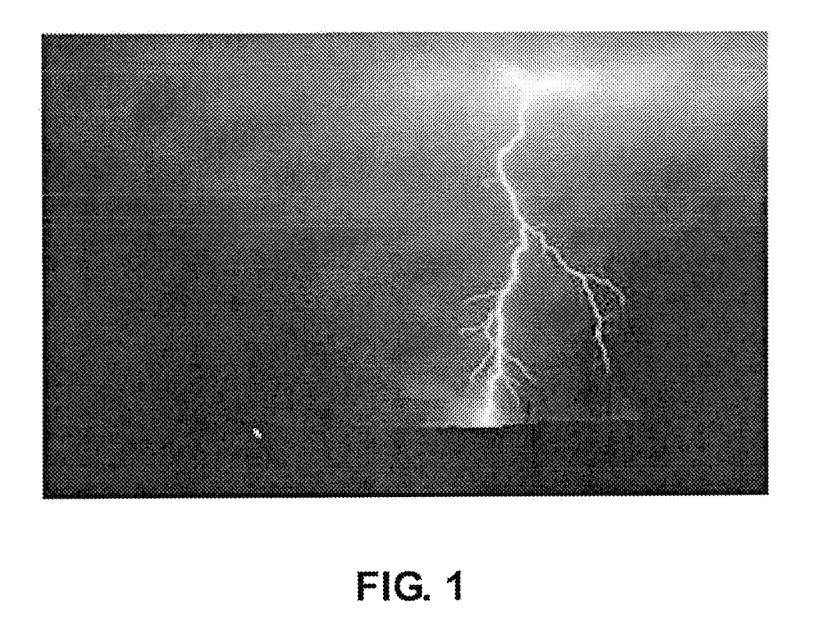
FIG. 1 depicts a lightning bolt.
Figure 2:
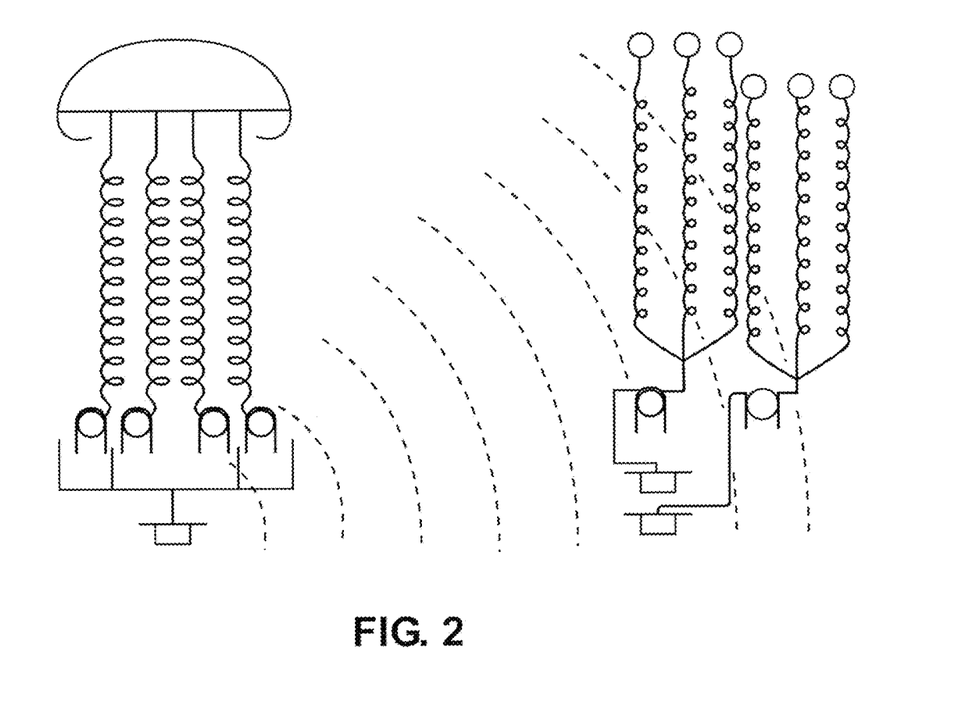
FIG. 2 depicts a Tesla device to converge the harmonic energy from four independent series resonant circuits.

This work inspired a small scale superluminal Coulombic field experiment by Obolensky based upon FIG. 2. In Tesla's application to facilitate phase-conjugate energy resonance and wireless transmission of energy, he wrote the following.

"The wave starts with theoretically infinite speed, slowing down first very quickly and afterwards at a lesser rate . . . . Only force is conveyed to all points of the earth, the energy itself traveling in definite paths determined beforehand, reaches the receiver without the lightest dispersion, so that an incomparably great amount is collected than is possible by radiation."

Also, Tesla's patent application's spherical wave phenomenology clearly parallels that envisioned by Louis de Broglie's in his double solution theory.

"The only way to understand what is going on seems to be to admit that the spherical wave emitted at the start does not remain spherical indefinitely. We can then say that the wave only has to remain spherical for a short time in order to be able to explain the success of the Schrodinger experiment"[xi] I.

This miniature Tesla magnifying Transmitter is within 320 cubic-foot (8'×8'×5') magnifying transmitter's hermetic enclosure, at a temperature of 90° F. and relative humidity of 85%, an apparent immediate temperature drop exceeding 9° F. occurs upon impulse modulating the elliptical dome's Coulombic Field. Obolensky used a Guilemin a-parameter, MathCAD, program which facilitated his design for the parabolic rise and fall, impulse modular needed to excite his 18' diameter elliptical-dome electrode. This earth/air capacitor-electrode is held 5' above its ground plain by the Diala-oil filler cylinder that contains and insulates the impulse modulator components.

Figure 4:
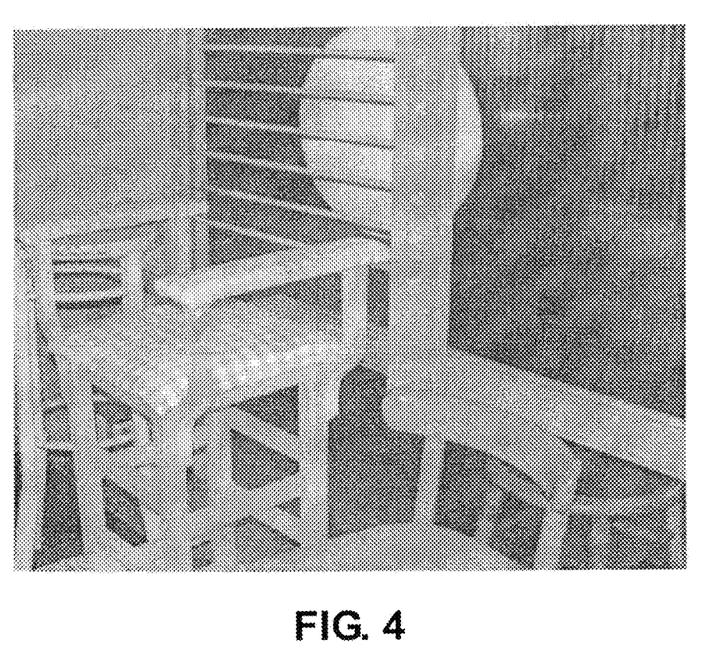
FIG. 4 depicts Obolensky's miniature Tesla Magnifying Transmission Instrument treatment room. Electro-magnetic shock waves in a controlled non-linear environment creates a phase-conjugate (time-reversal) replica, resonating with the human electro-magnetic field (human aura). It's use for the body's mitogenic entropy reduction has implications for medicine and science.

FIG. 4 shows Obolensky's miniature Tesla Magnifying Transmission Instrument treatment room. Electro-magnetic shock waves in a controlled non-linear environment creates a phase-conjugate (time-reversal) replica, resonating with the human electro-magnetic field (our aura). It's use for the body's mitogenic entropy reduction has implications for medicine and science.

In 1949, Obolensky worked for Dr. R. P. Shaw who was investigating toroidal-spin shock waves under the US Navy and Air Force "Project Squid" program. Shaw stated, while investigating macro-luminal shock waves, "If you create the right kind of magnetic field, you can punch a hole in the fabric of time." In Obolensky's miniature Tesla magnifying instrument, high voltage with spin-velocity exceeding Mach 5, the triple-converging shockwaves of a toroidal-spin soliton spins into a linear gas tube and then into a non-linear dome. This phase-conjugating virtual "mirror" reverses the entropy flow of energy structures entering the central Mach disk.

The warp and weft of this fabric is the accepted, thermodynamic equilibrium, entropy. Here, the time arrow points to increasing entropy and dispersion. However, the far from thermodynamic equilibrium Mach disk can reverse the direction of entropy flow so normal entropy and dispersion cancel.[xii]

"Experiments confirm the existence of mutual interaction between material systems by means of time. This interaction does not transfer the momentum, in other words it does not propagate but appears immediately in the other material system. In this way a immediate communication and information transmission appear to be possible."[xiii]

Evolved life utilizes immediate communication and information transmission. However, accepted science rejects this immediate action at a distance contention because conventional thinking prefers the Abelian mathematics of the standard, Maxwellian, U (1) Gauge symmetry. This symmetry convention facilitated commercialization of light-speed limited, Transverse-Electro-Magnetic (TEM) Hertz-wave technology. The SU (2) and higher dimension groups needed to support Longitudinal-Electro-Magnetic (LEM), Tesla-waves, all require complex non-Abellian mathematics.

The magnifying transmitter effect can be explained by the far from thermodynamic-equilibrium macro-luminal Mach disk. This effect was not realized until Prigogine won his Nobel Prize by proving that far from equilibrium thermodynamic process circumvent the second law of thermodynamic. In other words, as perfect information is normally lost over time all imperfect systems increase in entropy until they die. In this sense, disease is the immune systems inability to minimize entropy gain far from thermodynamic equilibrium.

The Magnifying Transmitter Organizes Water, Creates Emanations of Acupuncture Points, and Improves Disease Conditions The negative-ion wind produced by Obolensky's magnifying transmitter is created by a train of LEM solitons that negate otherwise entropic heat produced by the steam jets that keep the elliptic terminal wet. The ability of structured negative-ion wind to organize atmospheric water plays a significant role in the body's physical health. The average person loses between one-eight and three quarters pounds of toxic sweat, while well hydrated persons have lost 2 lbs. during a single treatment. Most remarkable several very dehydrated individuals have gained 2 pounds.

Figure 5:
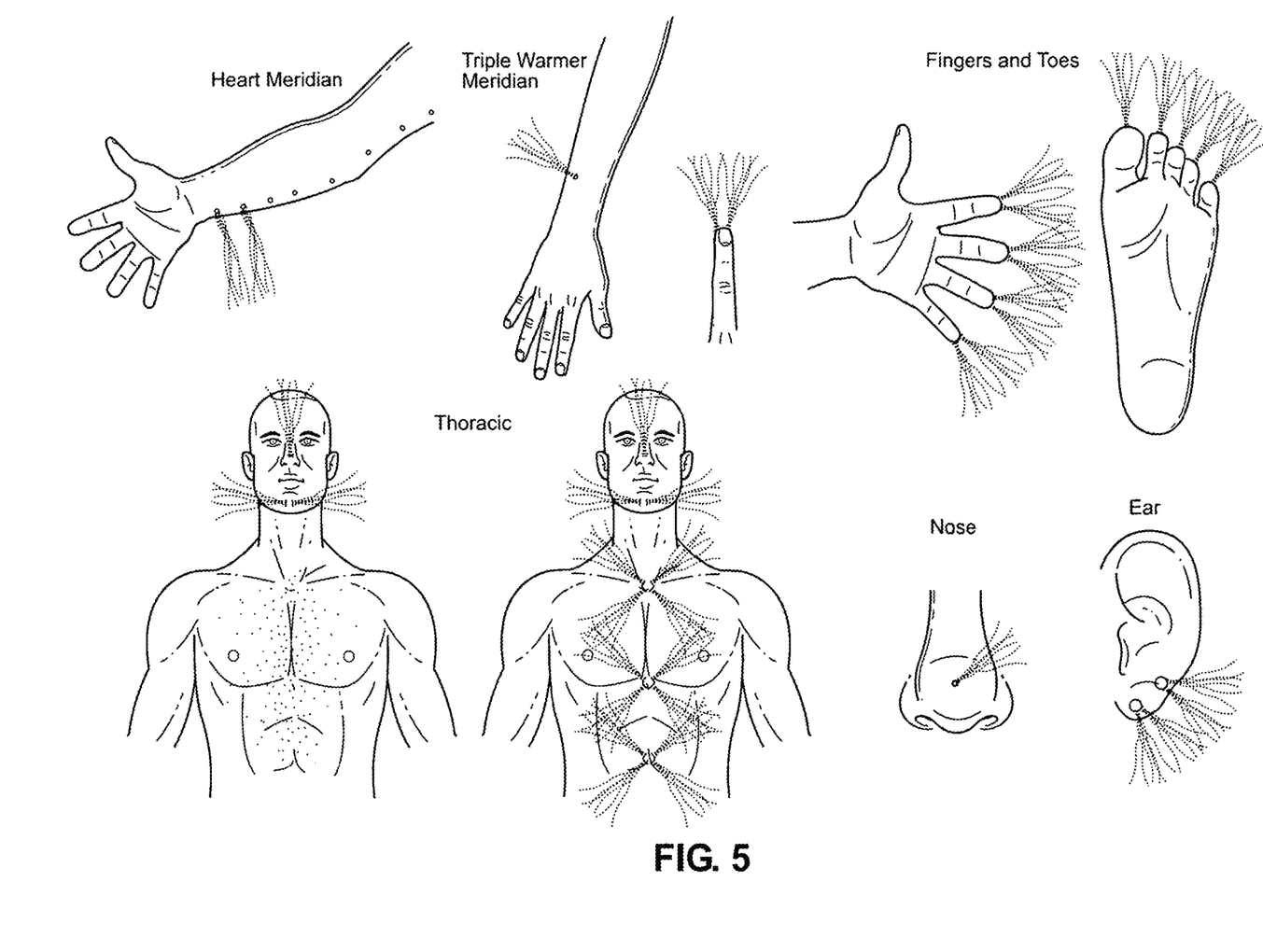
FIG. 5 is a diagram drawn inside the Negative Ion generator room reflecting the Traditional Chinese Medicine meridians and points of the Heart, Triple Warmer, Ren (thoracic), Ear and Nose points. Note the second thoracic picture appears to be the Yoga chakras 5.

FIG. 5 was sketched by inventor while inside the Negative Ion generator room reflecting the Traditional Chinese Medicine meridians and points of the Heart, Triple Warmer, Ren(thoracic), Ear and Nose points. Note the second thoracic picture appears to be the Yoga chakras.

Open circuits create illumination of acupuncture points and variation of beaming violet light. In complete darkness this equilibrium interaction can be seen activating the various acupuncture points on the surface of the skin. Individuals in contact with the instrument emanate white light from their fingers and toes and master acupuncture points throughout the body show approximate patterns, for example, the triple heater (posterior aspect of the forearm) or heart pathway points on the elbow and ulnar aspects of the arm. See FIG. 5. On the torso variations show up, in one case small points all over the torso and in another patient approximate to the Indian's yoga chakras. Beams of healing light play to and fro, directed entirely by the body's electromagnetic interaction with nanosecond-period Tesla-waves and the negative-ion wind they produce. Injuries, bone spurs, cancer tumors, diseased organs need no instruction from the instrument, positive ions in the body are bombarded with negative ions in a beam of variations of violet. (Szent-Gyorgyi 1988)

"Molecules do not have to touch each other to interact. Energy can flow through the electromagnetic field . . . . The electromagnetic field, along with water, forms the matrix of life. Water can form structures that transmit energy."

Improvements were recorded for tendinitis, ligaments, superficial cuts, bone spurs, edema, osteoarthritis, sinusitis, migraine headaches, and various cancer Shinnick, Obolensky, Haddad and Maize published clinical results from his miniature Tesla Magnifying Transmitter, as well as a discussion of electro medical research on bone spurs, and, tumors.[xiv] [xvi] Subject treatment for one organ, as for example, the skin or heart, saw immediate relief, but not lasting. Subsequent clinical examination found other organ problems such as the stomach or colon which affected the other disease organ area. This organ interaction and imbalance will be discussed later but is a significant understanding.

Bose-Einstein Condensation of Inorganic and Organic (Human Global Physiological Measurements)

Fröhlich showed that when energy is supplied to such a system, either from metabolism or from external sources above a critical rate, it is automatically channeled into the lowers frequency mode, thereby resulting in coherent excitation of the vibratory components (a phenomenon known as Bose-Einstein condensation). Fröhlich predicted, on the basis of quantum mechanics that the living matrix can produce laser-like coherent beams at many wavelengths including visible and near visible light that is radiated into the environment. These are not subtle phenomena they are large scale and their effects are not trivial. For example, living tissue is so highly organized that it can support the Bose-Einstein condensate and excitation of Fröhlich resonance.

Figure 6:
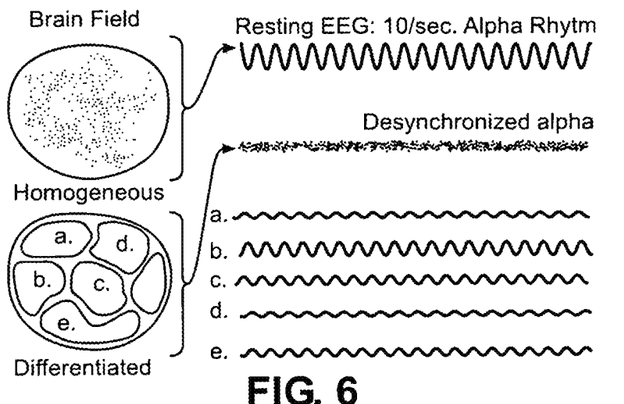
FIG. 6 depicts the synchronization of brain waves during meditation.
Figure 7:
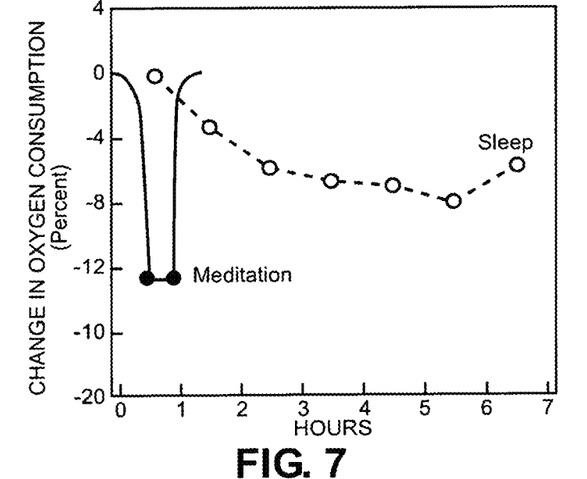
FIG. 7 depicts a chart comparing oxygen consumption during Zen Meditation and during sleep.
Figure 8:
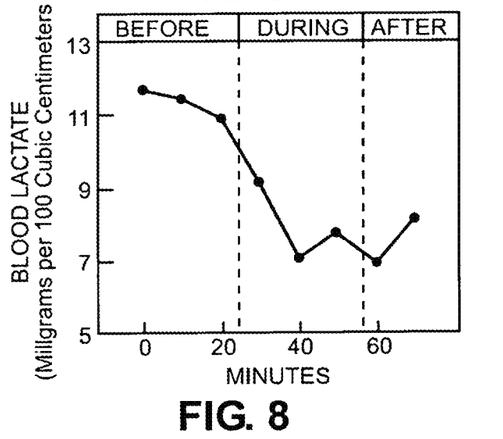
FIG. 8 depicts blood-lactate changes associated with Zen Meditation.

FIGS. 6, 7 and 8 show the synchronization of brain waves during meditation; the comparison of oxygen consumption during Zen Meditation and during sleep; and blood-lactate changes associated with Zen Meditation, respectively, of a Zen Master meditator in the deepest states of meditation or the Bose-Einstein state. {{Two types of meditation will be discussed here, Involuntary like Zen meditation where one does not use the Will and voluntary muscles to move the breath and Qigong where volition or will is used to recruit the voluntary muscles.} }

What one sees in the Bose-Einstein most stable states in Zen meditation is an abrupt change in brains waves, oxygen consumption and blood lactate.$^{\{xvii\}}$ Both inorganic and organic systems have a potential for a stable Boss-Einstein conjugate states$^{\{xviii\}}$. Inorganic gas, by lowering temperature, and organic beings, when mentation stops and the synchronization (organs as well) of the mental and body functioning settles both show similar properties. Juxtaposition parallel properties in the process to conjugate states between organic (enlightenment) and super fluid helium 4He II shows these properties of oneness.

1. State of Oneness of high stability and coherence
2. Extreme low-noise levels
3. Results from abrupt transition between states
4. Active solely in the present, the Now free of reactivity from the past, free of memory
5. Transcend duality between opposites
6. Respond as Oneness and appropriately to stimulus and pressure
7. Transmit information of exceptional clarity
8. Display behavior to 'ordinary' man as "strange", generally expressing liberation from ordinary constraints.
9. Basic states (at 'zero' noise levels) consistent inherently of both stationary and moving aspects.

Myogenesis starts at conception but is mitigated by outside culture and bifurcates into adjustment to Nature's conditions in behavior and mentation, or afferent sympathetic reaction to outside the organism. Chinse medicine see six pernicious weather influences, heat, cold, dampness, dryness, wind, summer heat. This creates habits of behavior and mentation which here will be defined as inertia (stagnation) for disease from organ and mental reactivity. In weather influences not adjusting to climate changes. Anaplasia can happen under these fragmented diseased states where cells revert back to primitive embryonic state of undifferentiated fast-growing cells, such as cancer. Afferent conditioning from outside trauma affects organ functioning and creates a lack of synchronization that is reactivated by approximation of original trauma based upon physiological experiments. How does one get to an unconditioned state and not knee-jerk reactivity to cultural and individual fragmentation, or not adapting to weather.?

Curvilinear and transverse phenomenon can be seen in the very structure of the human skull, and the transverse up and down of the nervous (motor) system, immune system, blood (oxygenated and deoxygenated), and the in and out of the respiration of the cell and lungs. Organs and the heart can be conditioned to be out of synch by cultural and individual differences as well as habits of food and substance intake.$^{\{xx\}}$ We tested this in chronic heart disease by Qigong meditation practice which resulted in a synchronization of body physiology in terminal phases of heart disease to increase heat, and calm an agitated state. In cocaine addiction women were found to be receptive to continue practice of Qigong meditation than men to stabilize the lack of habit over a longer period.$^{\{xxi\}}$ However men still did better than conventional addition therapy.

European Science does not have a Philosophical History of Curvilinear and Rectilinear Understanding of the Human Mind/Body Consciousness to the Aether Field, Internal Organs and Energy Flow within the Body. Turning to the Orient.

We have shown non-zero mass and spin-1 in the aether (inertia coupled with gravity to maintain coherence), the Tesla diagram for his patent showing curvilinear and transverse creating negative entropy, the earth's cavity and transverse lightening producing negative ions for human life, Obolensky's miniature Tesla inspired Magnifying Transmission instrument and adiactic reversal of disease in clinical research and the measurement of superluminal velocity. Also, we showed reversal of disease in heart disease and cocaine addiction through Qigong meditation. Research in this area with be presented and hypnosis of a circular Domal acupuncture area (not a point) both inside and outside the body.

Philosophically Kashmiri Tantrism in ancient time replaced linear logic with spherical or non-dual logic. In this way things are not defined in a particular way or spatial fixation but end up merging into the One. Sadness is a prelude to joy and the creation/destruction of the universe is a process of perpetual cycle, as does birth and death returning to absolute consciousness. Thinking this way there is no longer a break in the fluidity of motion. This means humans are caught between the beginning and end of a thought process. It is a none-ending process. Body/mind is a physical experience. Emotions felt are experienced in the body. Duality is a process of contraction. Clinical experience sees patients, migraines for example, as a constriction of the circular head. The contraction eases when energy is added, and expansion opens providing more space and an ability to relax. Acupuncture does this with its perpendicular insertion, as does mechanical manual pressure, Qigong (not touching the body), laser, or motion, even heat. When this happens, thoughts are no longer limited, and space opens up in the mind. Thoughts/body become spherical because what is inside is outside, and outside is seen as part of the mind/body. Phase conjugate can happen out of a habituated physiological state by stark awareness, meaningful words, or, seeing an event triggering a phase shift spontaneously.

Figure 9:
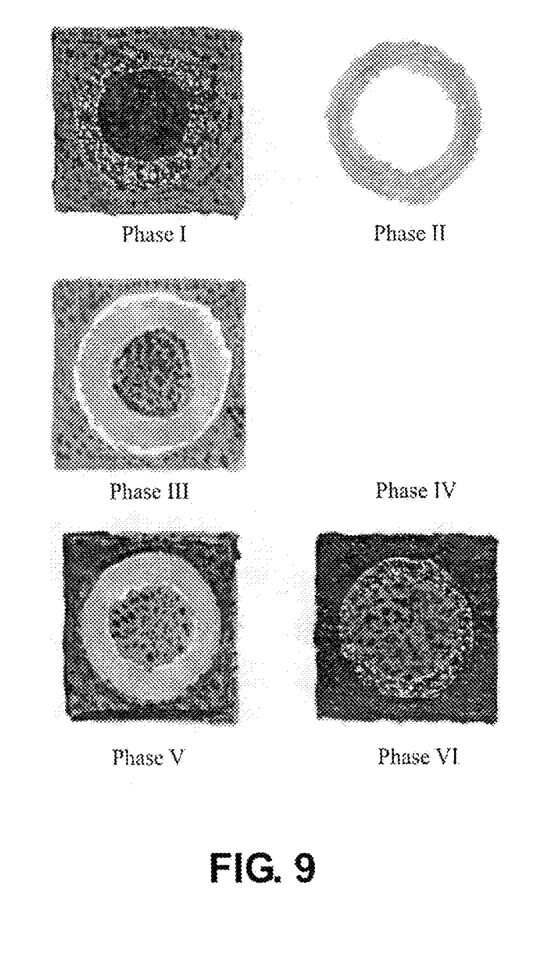
FIG. 9 shows the contraction and expansion of an acupuncture area.
Figure 10:
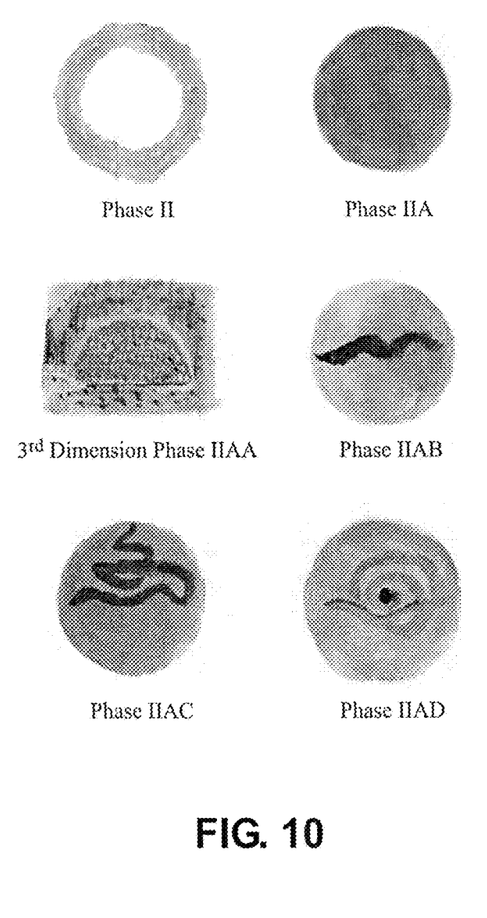
FIG. 10 depicts the transverse quanta of energy entering and moving in many directions.

In a research project with Yoshiaki Omura, M.D., D.Sc and electrical engineer, while examining the acupuncture points in the late 1980's, were found not as a point but an area. Closer examination showed upon stimulation the opposite, of biochemically constriction, became a biochemical relaxation response.[xxii] [xxiii] Acetylcholine, serotine, methionine-enkephalin, beta-endorphin, ACTH, secretin, cholecystokinin, norepinephrine, and GABA were found on all acupuncture points and along the meridians regardless of the meridian. Extensive biochemical changes happened instantly throughout the body. A high-powered light on the finger nail shows an immediate vasodilation of the small capillaries. Inventor continued this study and found that the area above the acupuncture point went through continuous contraction and expansion every second, through six phases. Also, toxic conditions to the organ shift the organ pathway. The heart and diaphragm have multiple phases and pathology happens when one phase is stuck or constricted. In the heart the thoracic rib cage locking, in the diaphragm, and the back of neck twisting. Life goes on but morbidity sets in. FIG. 9 illustrates the contraction and expansion of the acupuncture area. FIG. 10 illustrates the transverse quanta of energy entering and moving in many directions.

Individuals in disease spent more time, a fraction of a second more in one phase and are phase stuck. These domals areas raise about the body surface. These domals are in the field outside the body. The domal is shrouded in a blue canopy with underlining hexagonal structure, inside is a spatial density matrix UQi area, the other half penetrates inside. With energy stimulation (acupuncture, Qigong, laser, manual stimulation) after a flushing of a pure color, triggers Phase II. A quantum of energy moves through the domal transversely or spinning up or down.

This understanding came from 300 clinical cases of different diseases over five years and resulted in these mind images from this long clinical research. To be sure, organs are solid (liver, kidney, pancreas, heart) or hollow (gall bladder, bladder, stomach, lungs, large intestine and small intestine) with the hollow organs having transverse movement such as bile, water, food and digested food. The solid organs filter substances and the heart with its electro cardiac cells create rhythm for the arteries to contract and circulate blood. The heart has more than one direction, going up to the head and down to the body. Movement of de-oxygenated blood against gravity back into the heart and lungs through the veins is dependent upon body movement. Veins have trap doors to prevent backflow but need movement to overcome gravity.

Gravity is a major impediment to blood circulation to the head (average 80-90 mmHg) and up from the feet (180-190 mmHG). Gravity and inertia define mass so impediment to energy flow is culture/outside/weather conditions habitual physiological functioning and mental habits. In other words, the dome acupuncture areas can get stuck in a phase with disease perpetuation and the body/mind as a whole conditioned and phase stuck. Inertia and stagnation create reactive condition of fragmentation or better put maintain condition. What are the Ways that the Fragmented Physiological and Mental Habits can be Changed to a More Unconditioned or Phase Change Natural State?

Qigong's curvilinear and up and down transverse practices create a conjugate phase change and capture space filled substance defined as density matrix, uncreated, unformed and named here as Universal Qi or UQi. Our created form of the mind/body is conditioned and bifurcates into organ interaction dysfunction and mental fragmentation. In Zen meditation one just sits still for a long period and does nothing just waits, not attaching to thoughts, letting them go, then things settle over time, with no Will or volition.

Inside, Up and Down

Qigong uses Will and internal practices to create Qi by synchronizing organs from fragmented yin and yang organ struggle by internal up and down with the breath. Humans have a left and right side and when one dominates, the spine suffers. This happens from spine tension (posture) which compromises enervation of the organs. Front and back go together. Hollow Organs are Yang and solid Yin. Together harmonized and create Qi. Qi creates the conjugate state phase change. This is not the normal state, mostly there is disequilibrium with pain and suffering with morbidity lurking. Qigong practices help create internal Qi from out of balance Yin and Yang organs.

Outside to Inside and Inside to Outside.

Figure 11:
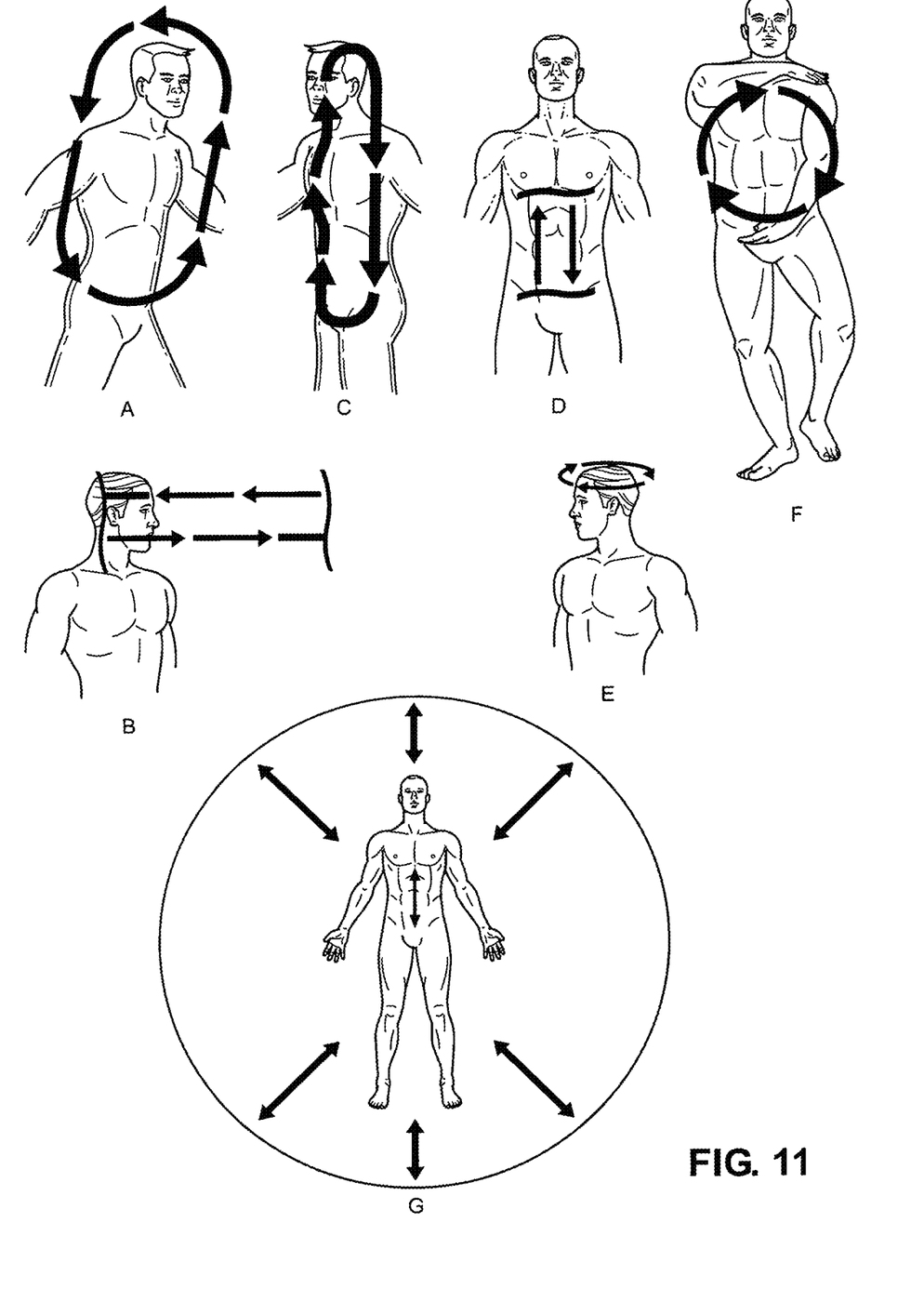

Lorentz's statement that the aether and elements were also in measurement instrument (the acupuncture dome is inside the body as well) is a convergence with Oriental Natural philosophy's understanding the body and the Cosmos are made up of similar elements, Qi. The most implicit assumption is that this Universal Qi and internal Qi (bifurcated into yang and yin through fragmentation) can be accessed through up and down practices between areas of the body regulated by breath flow. Also, Universal Qi (density matrix non-zero matter and spin-1) can be accessed through practices of bringing in outside universal Qi through the breath. FIG. 11 shows the various internal and external practices.

FIG. 11A is the microscopic external orbit. FIG. 11B is gathering UQi externally. FIG. 11C is the internal microscopic orbit to regulate Qi inside the body. FIG. 11D is internal transverse meditation to regulate the fire organ, liver, with the lower water organ, bladder to harmonize. FIG. 11E is transverse inner skull cavity meditation.

FIG. 11F is the practice of Ba Gua Yi Qui Gong which creates (Xin) information about the relationship between the Universe, Nature, and Humans. Curvature Sky/Yang and Rectilinear Earth Qi Yin harmony resides in the ball. The practice is with Yi intension and Nian mind (ling soul) focusing on the center of the ball, spinning it with palms shoulder width and ball from top of chest to waist. Left to right, up and down, around. (This is the essence of Tai Chi Chuan) This then creates a pattern that teaches Nature's way of the circle and transverse processes.[xxiv]

FIG. 11G is breathing in through all the pores from 360 degrees then entering the body traversing up and down the abdomen before breathing out again. This harmonizes the internal organs and brings in UQi and is curvilinear and transverse practice all at once.

FIG. 13 shows an oscilloscope image measuring light speed from co-axial sensors within the miniature Tesla Magnifying Transmission in 2004. This shows a superluminal velocity, then variations in speed.

SCOPE OF INTELLECTUAL PROPERTY

The reader is respectfully directed to the Copyright Notice located near the beginning of this document.

All trademark, service mark, and similar rights in and to any name, term, phrase, logo, graphic, mark or otherwise, appearing herein, including but not limited to those explicitly so marked, that are not the property of others, are hereby reserved to the inventor.

The intended scope of the instant invention also includes the combination with other related technologies, now in existence or later developed, which may be combined with, or substituted for, elements of the instant invention.

It will thus be seen that the objects set forth above, among those made apparent from the preceding description, are efficiently attained and certain changes may be made in carrying out the above method and in the construction set forth. Accordingly, it is intended that all matter contained in the above description or shown in the accompanying figures shall be interpreted as illustrative and not in a limiting sense.

Now that the invention has been described, what is claimed as new and desired to be secured by Letters Patent is:

END NOTES i. A. G. Obolensky and J. P. Vigier. "Preliminary observation of the superluminal propagation of the Coulombic field support Lorentz's interpretation of Special Relativity Theory." Whole Person Healing Institute, Inc. Blue paper. This a presentation of their article based upon discussions before their deaths with subsequent implications for self healing.

ii. A. Einstein., Ann. d. Phys. 17 (1905), 891.

iii. H. A. Lorentz. Proc. Aca. Sci. Amst. 6 (1904), 809 iv. J. P. Vigier, Phy. Lett. A 235 (1997), 419.

v. T. Carey, "Which Special Relativity is correct—Einstein's or Lorentz's?" preprint (1998)

vi. M. V. Mesquita, A. R. Vasconcellos and R. Luzzi. "Considerations on Undistorted-Progressive X-waves and Davydov Solitons, Frohlick-Bose-Einstein Condensation, and Cherenko-like Effect in Biosystems." Brazilian Journal of Physids, Vol. 34. No. 2, June 2004 vii. C. K. Thornhill. "The Kinetic Theory of Electromagnetic Radiation. Speculations in Science and Technology Vol. 8, No. 4, Pages 263-272 viii. T. V Flandern and J. P. "Vigier Experimental Repeal of the Speed Limit for Gravitational electrodynamic, and Quantum Field Interaction." Foundation of Physics, Vol. 32, No. 7, July 2002.

ix. B. Margon. Sc. Am., 243, No. 4 (1980), 44 x. R. Antanasijevic, R. Banjanac, A. Dragic, et al. "On the Electrical Discharge in Air." Institute of physics. Pregreicia 118 Zemun, 11980 Belgrade, Yugoslavia and J. P. Vigier CNRS/UPMC, URA 769, Gravitation et Cosmologie Relativites. Tour 22012, 4e etage. Boite 142, 4 Place Jussieu, 75005 Paris France.

xi. Louis de Broglie. Cahiers de Physique. No, 147, October 1962. Pp. 425-445.

xii. Guy Obolensky and P. Shinnick. "Basics of Toroidal Spin Shock Waves." Whole Person Health Summit and Second Qigong Summit, Baltimore, Marhland. Apr. 14-17, 2005.

xiii. N. A. Kozyrev. "Possibility of Experimental Study of the Properties of Time". USSR/USA Joint Publication Research Service. 1000 North Glebe Road, Arlington, Va. 22201 xiv. Alexander Guy Obolensky, Phillip Shinnick, Joseph P. Maize. "A New Multidisciplinary Approach to Electro-Medicine Research." Jour Sci Heal Out. Vol 4, No. 14-15, 2012.

xvi. J. Haddad, G Obolensky, P. Shinnick. 'The Biological Effects and the Therapeutic Mechanism-of-Action of Electric and Electromagnetic Field Stimulation on bone and cartilage: New findings and a Review of Earlier Work.' Jour of Alt and Com Med. June, 2010.

xvii. P. Shinnick and S. Freed. "A Case Study of the Synchronization of Human Energy in an Acute Condition of Chronic Heart Disease Through Complementary Treatment." Sub Ener & Ener Med. Vol. 13, No. 3., 2004.

xviii. P. Shinnick and S. Freed. "Organic Life energy in Physiological States of Chan) or Zen) Buddhism and Inorganic Analogous States of Super Fluid Helium Liquid." Jorn Sci Hea Outcomes. Vol 3 No. 12, July, 2011 India.

xix. K. M. Bykov, G. Y. Vladimirov, V. Y. Delov, G. P. et al. Text-Book of Physiology, Foreign Languages Publishing House. Moscow. 1958. A. R. Luria. "The Problem of the Cultural Behavior of the Child." From the Psychological Laboratories of the Akademii Kommunisticheskoga Fospiitaniyu im. N. K. Krupskai Journal of Genetic Psychology. Vol. 35 Clark Union 1928.

xx. A. A. Volokhov. "On the Significance of Various Levels of the Central Nervous System in the Formation and Development of Motor Reaction in Embryogenesis." Plzen. Lek. Sbor., Suppl 3: 141-145, 1961.

xxi. Chen, K, Ziedunis, D. Comerford, A, Shinnick, P. "A Pilot Study of Introducing Qi-Meditation Therapy into Addiction Treatment. Journal of Addictive Diseases, 2005.

xxii. P. Shinnnick and A. Borgna. Whole Person Healing The O-Ring Imaging Technique Influences to Oriental and Occidental Medicine. AuthorHouse. Bloominton, Ind. 2009.

xxiii. P. Shinnick and L. Porter. Whole Person Self-Healing: A Science and Art. Bentham Scientific Publishers. UAE. 2017 xxiv. W. Li Ping. Ling Bao Tong Zhi Neng Nei Gong Shu. Translated by Richard Liao. No publisher listed. ISBN-13: 978-1470174545

The invention claimed is:

1. An apparatus for creating an energetic field to promote energetic healing comprising:
 a. a first enclosure containing electrical components further comprising at least a transformer and coil bathed in dielectric oil;
 b. a gas-filled glass tube through which an accelerated modulated energetic current is induced at a first end by the action of the electrical components of element a., thereby inducing an energetic field that is, at least in part, available at a second end of the gas-filled tube;
 c. a second metal-lined enclosure sufficiently large to contain a patient and, optionally, a therapist/practitioner;
 d. an opening in said second enclosure through which the second end of said gas-filled glass tube passes into said second enclosure;
 e. optional seating/support components to position said patient with respect to said energetic current and field.

2. The apparatus of claim 1 comprising, in addition:
 f. a baffle positioned between the second end of said gas-filled glass tube and said patient to disperse the accelerated modulated energetic current exiting from said second end of said gas-filled glass tube.

3. The apparatus of claim 2 comprising, in addition:
 g. that said baffle is substantially circular.

4. The apparatus of claim 3 comprising, in addition:
 h. that said baffle is further concave and oriented such that said second end of said gas-filled glass tube points into said concavity.

5. The apparatus of claim 4 comprising, in addition:
 i. that said baffle is further covered with a tightly woven fabric.

6. The apparatus of claim 2 comprising, in addition:
 j. a plastic sheet positioned between said baffle and said patient in order to prevent arcing between said baffle or tube and said patient.

7. The apparatus of claim 6 comprising, in addition:
 k. that said plastic sheet is infiltrated with nano-particles.

8. The apparatus of claim 2 comprising, in addition:
l. that the atmosphere within said second metal-lined enclosure is maintained at a temperature of substantially 90 degrees F. and a humidity of substantially 85%.

9. An apparatus as in claim 1 wherein said current of clement b. spins.

10. An apparatus as in claim 9 wherein said spin is toroidal.

11. An apparatus as in claim 2 wherein said current of element b. spins.

12. An apparatus as in claim 11 wherein said spin is toroidal.

13. A method for promoting energetic healing comprising:
   a. Placing a patient into the metal-lined enclosure, and exposing said patient to the energetic field, of an apparatus comprising:
      i. a first enclosure containing electrical components further comprising at least a transformer and coil bathed in dielectric oil;
      ii. a gas-filled glass tube through which an accelerated modulated energetic current is induced at a first end by the action of the electrical components of element i., thereby inducing an energetic field that is, at least in part, available at a second end of the gas-filled tube;
      iii. a second metal-lined enclosure sufficiently large to contain said patient and, optionally, a therapist/practitioner;
      iv. an opening in said second enclosure through which said second end of said gas-filled glass tube passes into said second enclosure;
      v. optional seating/support components to position said patient with respect to energetic current and field;
      vi. a substantially circular concave baffle positioned between the second end of said gas-filled glass tube and the patient to disperse the accelerated modulated energetic current exiting from said second end of said gas-filled glass tube oriented such that the second end of said gas-filled glass tube points into said concavity and that said baffle is further covered with a tightly woven fabric; and,
      vii. a plastic sheet infiltrated with nano-particles positioned between said baffle and said patient in order to prevent arcing between said baffle or tube and said patient.

14. The method of claim 13 comprising, in addition:
that said patient is positioned with respect to said energetic current and field to optimally promote energetic healing.

15. The method of claim 13 comprising, in addition:
that the patient is instructed/guided by said therapist/practitioner in mental and/or emotional practices including, but not limited to, counseling, meditation and/or visualization.

16. The method of claim 13 comprising, in addition:
that the atmosphere within said second metal-lined enclosure is maintained at a temperature of substantially 90 degrees F. and a humidity of substantially 85%.

17. The method of claim 16 comprising, in addition:
that said patient is positioned with respect to said energetic current and field to optimally promote energetic healing.

18. The method of claim 16 comprising, in addition:
that the patient is instructed/guided by said therapist/practitioner in mental and/or emotional practices including, but not limited to, counseling, meditation and visualization.

19. A method as in claim 13 wherein said current of element a.ii. spins.

20. A method as in claim 19 wherein said spin is toroidal.

* * * * *